United States Patent [19]

Waldeisen

[11] Patent Number: 4,717,384
[45] Date of Patent: Jan. 5, 1988

[54] PNEUMATIC HYPODERMIC SYRINGE POLE

[75] Inventor: Robert B. Waldeisen, Williamsport, Pa.

[73] Assignee: Pneu Dart Inc., Williamsport, Pa.

[21] Appl. No.: 3,517

[22] Filed: Jan. 15, 1987

[51] Int. Cl.$^4$ .............................................. A61M 37/00
[52] U.S. Cl. ..................................................... 604/143
[58] Field of Search ................ 604/143, 141, 140, 218, 604/130

[56] References Cited

U.S. PATENT DOCUMENTS

| | | | |
|---|---|---|---|
| 3,688,765 | 9/1972 | Gasaway | 604/143 X |
| 3,768,472 | 10/1973 | Hodosh et al. | 604/143 |
| 3,780,734 | 12/1973 | Wulff | 604/218 X |
| 3,840,007 | 10/1974 | Fish | 604/218 X |
| 4,103,893 | 8/1978 | Walker | 604/130 X |
| 4,243,036 | 1/1981 | Ott | 604/130 |

Primary Examiner—John D. Yasko
Attorney, Agent, or Firm—Sughrue, Mion, Zinn, Macpeak & Seas

[57] ABSTRACT

A pneumatic hypodermic syringe pole of first and second axially connected hollow tubes joined by a coupling cylinder supporting an axially slidable valve member including a hollow valve stem adapted to sealingly engage opening within the end of a hollow syringe body whose opposite end carries a needle. A plunger within the syringe separates the body interior into a drug injection chamber communicating with the needle and a second chamber capable of receiving gas under pressure for driving the plunger to displace a drug from the injection chamber. The first hollow tube operates as a handle for manual grasping and forms a pressurized gas storage compartment open to the axially displaceable valve member. The syringe is axially shiftable internally of the second hollow tube forming a syringe holder with the valve stem being positioned in the path of movement of the axially displaceable syringe. Upon needle penetration into the body of an animal the syringe displaces the axially shiftable valve member to permit a compressed gas charge from the pressurized gas storage compartment to drive the plunger within the syringe to effect drug injection. After injection, manually pulling on the handle causes the needle to be pulled from the animal body closing the valve member and terminating communication between the gas storage compartment and the syringe. The pressurized gas storage compartment contains sufficient pressurized gas to effect a relatively large number of drug injections upon sequential replacement of the hypodermic syringes until the gas charge to the pressurized gas storage chamber is fully depleted.

12 Claims, 8 Drawing Figures

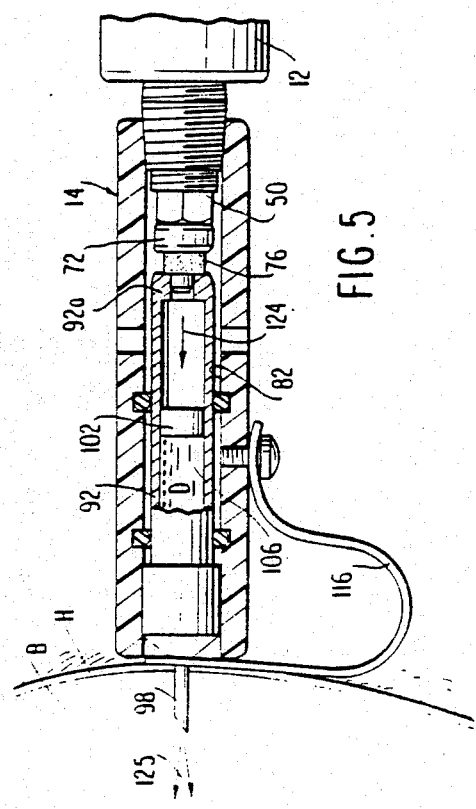

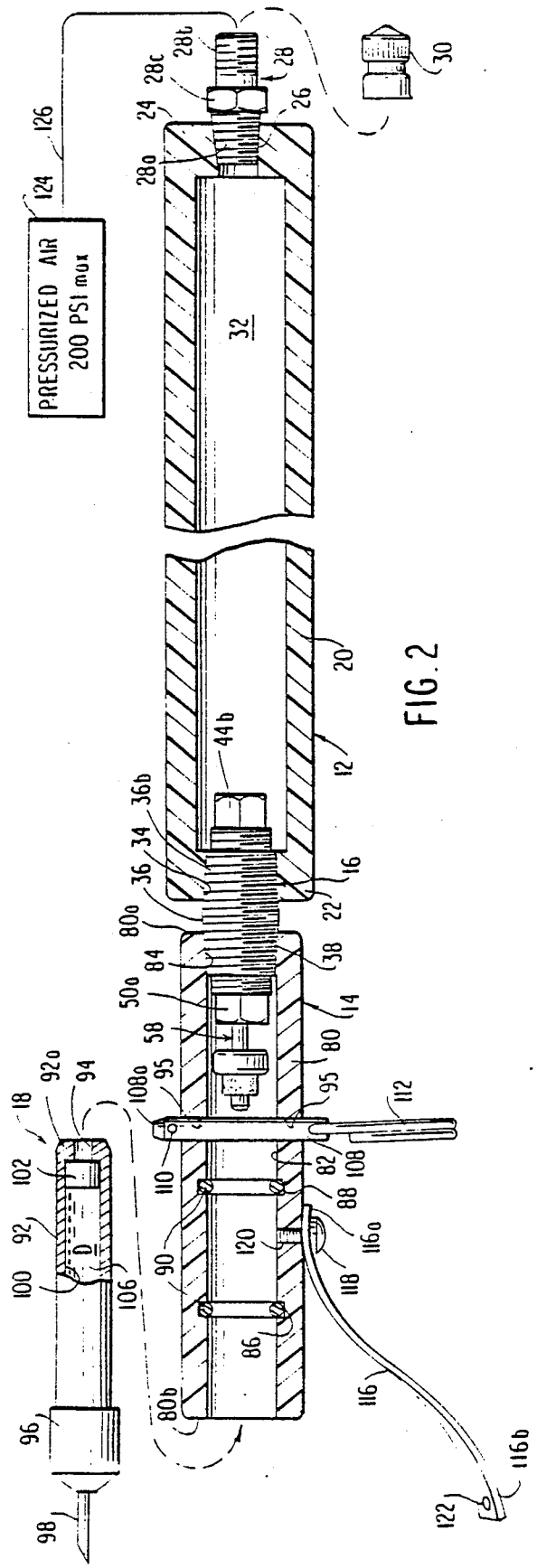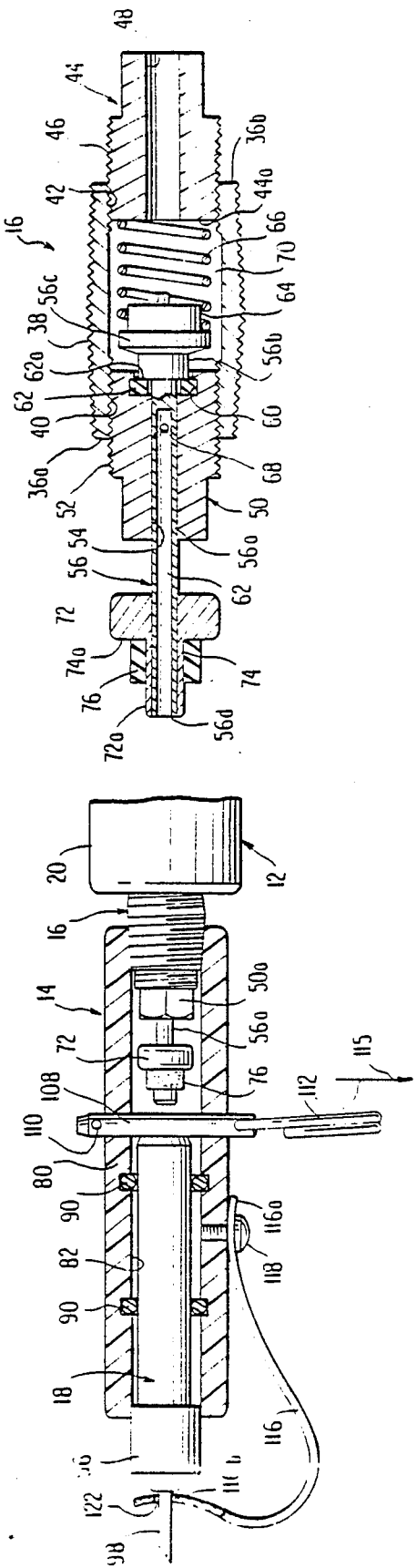

4,717,384

PNEUMATIC HYPODERMIC SYRINGE POLE

FIELD OF THE INVENTION

This invention relates to a compressed air driven hypodermic syringe pole for injecting an anesthesia or a drug into large, wild or domestic animals and more particularly to a hand held, tubular assembly for effecting momentary release of a portion of a stored volume of compressed air within a hand held tubular assembly for driving the plunger within the syringe in response to needle penetration of the animal hide to effect instantaneous injection.

BACKGROUND OF THE INVENTION

Conventionally, the injection of an anesthesia or a drug into large animals living in the wild or in zoos, has been achieved by utilizing an injecting projectile fired from a rifle or handgun. Such projectiles may take the form of a hollow, cylindrical casing which is subdivided into a pressure chamber and a drug chamber with a piston sliding within the casing and with the drug chamber terminating in a hollow needle. Such projectiles are fired at a certain, safe distance from the animal and the drug contained in the projectile is driven from the drug chamber by expansion of the gas (air under pressure) upon the projectile needle entering the body of the animal shortly after impact of the projectile. The following U.S. Patents are representative of such projectiles:

U.S. Pat. No. Re. 25,279, Crockford et al
U.S. Pat. No. 1,819,415, B. Harris
U.S. Pat. No. 3,358,685, C. A. Murdoch
U.S. Pat. No. 3,359,979, C. A. Murdoch
U.S. Pat. No. 4,103,893, E. C. Walker
U.S. Pat. No. 4,243,036, Ott U.S. Pat. No. 4,103,893 discloses a tranquilizer dart in the form of a hollow tube defining a cylindrical chamber having a tapered forward end mounting a pointed, hollow needle. A conical valve bears against an annular seat in the chamber with a triggering pin extending through the needle and having a forward end projecting beyond the needle point. Tranquilizer liquid is contained in the chamber between the valve and a first, front plunger. A rear plunger is provided at the rear end of the chamber with rearward movement limited by a transversely insertable stop pin. After loading a tranquilizing liquid into the frontal chamber, forward of the first plunger, air captured between the first plunger and the second plunger is compressed by insertion of the rear plunger. Upon impact, the triggering pin recedes, unsealing the conical valve and the expansion of the compressed air in the compressed air chamber forces the front plunger forward to inject the liquid into the animal.

U.S. Pat. No. 4,243,036 is directed to an automatically acting injection projectile which consists of a tubular casing bearing a slidable plunger and separating the interior of the casing into a rear gas chamber and a front anesthesia or drug chamber. A hollow needle projects forwardly of the tubular casing, a deformable tubular projectile brake surrounds the needle and the needle includes a radial outlet behind the needle point which is surrounded by a movable sliding sleeve. Upon impact with the body of the animal, the brake deforms and is pushed back along with the sleeve exposing the radial outlet of the hollow needle. The gas propellant drives the plunger to force the drug from the drug chamber through the hollow needle and into the surrounding tissue of the animal through the outlet.

While such systems have operated adequately in the past, and are indeed necessary because of the inability to closely approach wild animals, the same is not true for domestic animals. Irrespective of whether domestic animals or wild animals are to be injected, the use of a rifle or handgun fired automatic injecting projectiles is hampered by the single gas charge for the projectile and even though projectiles have been manufactured permitting a recharging of the gas chamber and the drug chamber, such recharging is difficult to achieve, particularly in the field.

Further, even where the large animals are of the domestic type such as cattle, sheep, etc. and can be readily approached, injection by single dosage, single use, hypodermic syringe projectiles, are beset by other problems such as premature injection of the drug during flight as a result of acceleration effect and inertia of the movable components.

It is therefore a primary object of the present invention to provide an extended length, pneumatic hypodermic syringe pole for use on animals which are readily approachable, such as domestic animals, or, on wild animals which are caged or otherwise restrained, which incorporates a large volume of pressurized gas capable of effecting multiple drug ejections, wherein the unit is easily handled, readily accepts prefilled syringes which can be quickly replaced and immediately used, wherein, the possibility of premature release of the drug is obviated and wherein, momentarily coupling of the pressurized gas source and the gas propulation chamber is automatically effected as a result of needle penetration of the body of the animal.

BRIEF DESCRIPTION OF THE DRAWINGS

FIG. 1 is a side elevational view of one embodiment of a pneumatic hypodermic syringe pole forming a preferred embodiment of the present invention.

FIG. 2 is a exploded, sectional view of the pneumatic hypodermic syringe pole of FIG. 1 and the replaceable hypodermic syringe employed therewith.

FIG. 3 is a sectional view of the forward portion of the syringe pole of FIGS. 1 and 2 with the replaceable hypodermic syringe mounted within the syringe holder.

FIG. 4 is a sectional view of the axial displaceable plunger assembly employed in the syringe pole of FIG. 2 and the coupling of the syringe holder to the gas tube.

FIG. 5 is a sectional view of the portion of the syringe pole shown in FIG. 3 at the moment of needle penetration into the body of the animal and during injection of the drug, during momentary connection of the gas chamber to the compressed air storage chamber of the gas tube.

FIG. 6 is a sectional view of a portion of the syringe pole of FIG. 2 illustrating the axial displacement of the plunger to effect communication between the gas tube and the compressed gas chamber within the syringe holder.

FIG. 7 is a longitudinal sectional view of an alternate embodiment of the invention utilizing a sealed gas cylinder within the gas tube.

FIG. 8 is a transverse sectional view of the gas tube of FIG. 7, taken about line 8—8.

DESCRIPTION OF THE PREFERRED EMBODIMENT

Reference to FIGS. 1-6, inclusive, show a first embodiment of the pneumatic hypodermic syringe pole indicated generally at 10, constituting an elongated cylindrical assembly of a gas tube indicated generally at 12, and a syringe tube or syringe holder indicated generally at 14 theradably connected by a threaded coupling or connecting assembly 16. As seen in FIG. 1, the syringe holder 14 supports at its forward end 14a a hypodermic syringe 18. It should be appreciated, that while the syringe pole 10 is formed of two detachably connected tubes or cylinders 12, 14, the unit may comprise a single tube, in which the forward, open end of such tube would be sized to receive a given diameter syringe 18. In the embodiments illustrated herein, purposely the pneumatic hypodermic syringe pole 10 is formed of two tubular sections which are coupled by a threaded fitting 16 so as to permit varying sized syringe holders 14 to be employed with a universal gas tube 12. Gas tube 12 carries a relatively large charge of high pressure gas such as air to facilitate the injection of a relatively large number of doses of drugs by the simple expedient of replacing the syringe 18 after each syringe use.

Reference to FIGS. 2-6, inclusive, shows the details of this embodiment 10. The gas tube 12 which may be formed of molded plastic as shown or metal, includes a cylindrical outer wall 20, closed off by end walls 22, 24. One end wall 24 is provided with a tapped axial bore 26 receiving the threaded end 28a of an inner tube type valve, indicated generally at 28, whose opposite end is threaded at 28b. A threaded cap 30 is carried by the threaded end 28b of the inner tube type valve 28. Valve 28, which is not shown in detail, bears a spring biased valve member (not shown) closing off air intake port permitting pressurized air up to 200 psi max to fill gas storage chamber 32, interior of the gas tube 12. The opposite end of the gas tube is also provided with a tapped axial bore at 34, which is threaded to one end 36b of a coupling cylinder 36. As seen in FIG. 4, the cylinder 36 is threaded on its exterior at 38 over its complete outer periphery while, the cylinder 36 is threaded on its interior only at opposite ends as at 40, 42. The upstream threaded end 42 of cylinder 36, threadably receives a cylindrical plug 44 via outer threads 46 and includes an axial bore 48. At the opposite end of cylinder 36, a valve seat member or plug 50 which is threaded at 52 on its outer periphery is threaded into the downstream threaded end 40 of cylinder 36. The valve seat member 50 includes an axial bore 54 which slidably carries a small diameter portion or valve stem 56a of an axial displaceable valve member, indicated generally at 56. The valve seat member or plug 50 is provided with a counter-bore at 60 which carries a plastic resilient ring 62 having an end face 62a, forming a valve seat for a radially enlarged portion 56b of valve member 56. Valve member 56 which is of elongated cylindrical form has a downstream axial bore 62 which extends from the downstream end thereof, almost to the radially enlarged portion 56b of the valve member. The valve member 56 terminates in a further radially enlarged portion 56c which is peripherally recessed at the upstream end thereof as at 64. Mounted about the recess 64 on portion 56c of valve member 56 is a coil spring 66 which is compressed between valve member 56 and end wall 44a of plug 44. Further, the valve member 56 is provided with one or more radial, air inlet holes 68 opening to bore 62 slightly downstream of the radially enlarged portion 56a of valve 56.

As may be appreciated, normally, the coil spring 66 provides sufficient force (in addition to the gas pressure within gas storage chamber 32) to maintain the valve member 56 closed relative on the valve seat 62a defined by the upstream face of ring 62. However, upon axial displacement of the valve member 56 to the right, FIG. 4, the valve stem 56a is displaced to the extent where the air inlet hole 68 opens to chamber 70 formed interiorly of the cylinder 36 and between end plugs 44 and at opposite ends of cylinder 56.

Fixedly mounted to the downstream end of the valve stem 56a is an annular stop 72 which is peripherally recessed at 74 at the end of stop 72 facing the syringe holder 14. About the recess 74 is provided a resilient seal ring 76 which may be formed of Teflon or the like. The seal ring 76 abuts a shoulder 74a defined by recess 74 on the stop 72. The seal ring is sized to closely fit the diameter of the recessed portion 74 of stop 72 and the seal ring has an outer diameter which is less than that of stop 72. Further, the outer diameter of the stop 72 is less than outer diameter of the coupling cylinder 36, at its downstream threaded end 36a.

As seen in FIGS. 2 and 3, the syringe holder 14 which may be formed of molded plastic, metal or the like is formed of a cylindrical body 80 having an internal bore 82. Bore 82 is provided with internal threads 84 on its upstream end 80a facing the gas tube 20 which receives the threaded end 36a of the coupling cylinder 36. The downstream end 80b of the syringe holder, includes, preferably, a pair of axially spaced internal circumferential grooves 86, 88 which carry resilient o-rings 90 which resiliently press against and maintain an axially inserted syringe body 92 of syringe 18 within the bore 82 of the syringe holder 14. Aligned holes 95 are drilled transversely through the syringe holder body 80 intermediate of the ends in position just forward of the downstream end 56d of the valve stem 56a of axially slidable valve assembly 58, with holder 18 coupled to gas tube 20.

Employed with the pneumatic hypodermic syringe pole 10 is a simplified form of a hypodermic syringe 18 wherein preferably, the syringe body 92 which is of cylindrical form, has an outer diameter which is slightly larger than the inner diameter of the two o-ring seals 90. The body 92 includes an integral end wall 92a which carries an axial bore 94 sized slightly larger than the outside diameter of recessed portion 72a of the stop 72 so that the downstream end of the stop 72 and the downstream end 56d of the valve stem 56a is positioned within axial bore 94. The seal ring 76 then abuts the end wall 92a of the cylindrical body 92 of the hypodermic syringe 18, FIG. 5. The syringe 18 terminates at its opposite end in a radially enlarged cap 96. Cap 96 integrally carries a hollow needle 98. Needle 98 terminates in a bevelled end. The needle has a small diameter axial bore (not shown) which opens to a bore 100 within the cylindrical body 92 of the syringe. Bore 100 carries an axially slidable cylindrical plunger 102. Plunger 102 closes off the bore 94 within end 92a of the syringe body 92. A mass of anesthetic, medicament or drug D fills the drug chamber 106 behind plunger 102. The injection hole through the needle 98 may be appropriately sealed off by conventional means to prevent loss of the drug D from injection chamber 106 prior to penetration of the needle 98 into the body of the animal.

A radially removable detent pin 108 having a diameter sized slightly smaller than the diameter of the transverse holes 95 through syringe holder body 80 is manually inserted into the aligned holes 94. The stop pin 108 has a beveled insertion end 108a and carries a radially projecting spring biased detent pin ball 110 near the beveled end which locks the stop pin 108 after insertion. The opposite end of stop pin 108 carries a ring 112 permitting manual removal of the stop pin prior to use of the syringe pole 10, by pulling on ring 112, FIG. 3 as per arrow 115.

It should be noted that the components of the materials of the embodiment described above is formed of tubular components consisting of high pressure PVC tubing or the like and with all fittings except for valve member 56 being standard plumbing components of brass or other metal, rubber o-rings, Teflon sleeves, etc.

In that respect, the inner tube type of valve 28 has a tubular outer body with an axially centered peripheral portion of hexagonal configuration as at 28c to facilitate coupling to the threaded bore 26 of gas tube end wall 24 by means of a standard wrench. Further, the end plugs 44, 50 have squared outer peripheral surfaces 44b, 50a, respectively, so that these parts may be threaded into the threaded ends of the coupling cylinder 36 using such wrench.

To prevent dislodgement of the syringe 18 after penetration into the bore 82 of the syringe holder 14, a flexible leather, plastic or like material strap 116 has one end 116a fixed to the outer periphery of the syringe holder body 80, FIG. 3, by means of screw 118 which is received within a tapped hole 120 within that body. The opposite end 116b of the strap 116 is provided with a small diameter hole 122 sized slightly smaller than the outer diameter of needle 98 so that it can be slipped onto the needle so as to frictionally couple the needle to the strap end 116b to complete a loose connection between the needle end of the syringe 18 and the syringe holder 14. Sliding of the syringe 18 within the syringe holder bore is then limited. As may be appreciated, prior to use of the syringe pole 10, the gas storage chamber 32 is charged to a suitable high gas pressure by making a connection between a pressurized air source 124, FIG. 2, via a suitable hose 126, and the inner tube type vale 28. A bicycle hand pump may constitute the pressurized air source 124. The gas storage chamber 32 of the gas tube may be filled readily at a gas station or the like having an available pressurized air source.

By placement of syringe 18 axially into the downstream end of the syringe holder 14 and with the strap 116 in place as shown in FIG. 3, the syringe pole 10 is ready for use. Just prior to manual, hand operation of the syringe pole 10, the stop pin 108 is pulled outwardly of the aligned holes 95 of syringe holder body 80 with the syringe in place as shown in FIG. 3.

The injection of the drug charge is accomplished as seen in FIGS. 5 and 6. The gas tube 12 is grasped much in the manner of a cattle prod and the needle 98 manually pressed into the body B of the animal, FIG. 5, with needle 98 penetrating the hide H. The pressure necessary to effect needle penetration into the body B is sufficient to displace the syringe body 92 to the right, FIG. 5, unrestricted by the stop pin 108 (which is previously removed). The syringe 18 moves relatively freely in axial bore 82 of the syringe holder 14 until the end wall 92a of the syringe body 92 contacts the Teflon seal ring 76 mounted on the stem 56a of valve assembly 58 via the stop 72. At this point, the downstream end 56d of the valve stem 56a projects internally of the axial bore or hole 94 of the syringe body 92. Continued movement of the syringe 18 from left to right, FIG. 5 is resisted by the coil spring 66 compressed between the head 56c of valve 56 and end plug 44. However, this bias is overcome and the valve member 56 shifts from left to right to the extent that, as shown in FIG. 6, the radial air inlet hole or holes 68 are open to the air chamber 70 within threaded connector 16. Chamber 70 is continuously open to the gas storage chamber 32 via the bore 48 within end plug 44. Some of the compressed air at approximately 200 psi rapidly expands through the hollow portion of the valve stem 56a via bore 62 placing the surface of plunger 102 at the pressure of the air stored within gas storage chamber 32. The plunger 102 is rapidly displaced to the left under the force of the expanding air as indicated by arrow 124, FIG. 5 driving the liquid drug D from the injection chamber 106 through the hollow needle 98 and into the body B of the animal, as per arrows 125.

Injection continues until all of the drug is dispensed from injection chamber 106 with the plunger bottoming out to the left end of chamber 106. This action takes a matter of seconds as long as the operator maintains pressure through the gas tube 20 against the body B of the animal. The operator manually pulls back on the gas tube 12 removing the needle 98 from the body B of the animal. The coil spring 66 then expands driving valve member 56 to the left and the radial hole 68 shifts to the left where it is sealed off by bore 54 within end plug 50. Additionally, the radially enlarged portion 56b of the valve 56 abuts the resilient sealing ring 62 forming valve seat 62a for valve member 56 to prevent possible loss of further air from the gas storage chamber 32 of the gas tube 12.

The operator removes the syringe 18, replaces the stop pin 108 and then replaces the used syringe 18 with a new syringe having a full drug charge D within its injection chamber 106.

Depending upon the diameter and length of the gas tube 12, the size and displacement of the syringe 13, the pressurized air (or other gas) charge within the gas storage chamber 32 may accomplish a relatively large number of injections without the necessity of gas recharging until the pressurized gas is nearly depleted from the gas storage chamber 32. Where the gas tube 12 functions as the handle and has a diameter of one inch, a length of 48 inches and where the gas storage chamber 32 is pressurized with 80 pounds of air pressure there is sufficient available air pressure capable of emptying at least 21-1½ cc charge volume syringes 18. Such syringes 18 can withstand pressures up to 200 pounds per inch. As may be appreciated, the apparatus uses a reusable syringe, that is mounted for sliding within the syringe holder 14. Automatically when the syringe needle is pushed into the animal A the opposite end of the syringe engages valve stem 56a shifting the valve member 56 so as to release some of the compressed air to the back of the syringe plunger or piston 102 via radial air supply hole 68.

The "shot" of pressurized air or other gas moves the plunger 102 rapidly forward in the syringe making an instant injection of the drug charge D within the injection chamber 106 through needle 98. With the air powered syringe quick injection can be made of animals which are not easily handled and the apparatus uses syringes which are prefilled for immediate use. Syringes of 1 cc to 10 cc capacity may be employed. The apparatus advantageously permits ready disconnection of the syringe holder 14 from the gas tube 12 (handle) when necessary to accommodate a larger size or smaller size syringe holder capable of receiving, holding and operating syringes sized to the 1 cc to 10 cc charge, for instance.

Reference to FIGS. 7 and 8 show a second embodiment of the invention in which there is modification of the gas tube; all other components of the syringe pole being identical to that shown in FIGS. 1–6, inclusive. In this case, the pneumatic hypodermic syringe pole indicated generally at 10' has a modified form of gas tube indicated generally at 12' coupled to the syringe holder 14 through a slightly modified connecting assembly 16. The modification to the connecting assembly 16' consists in drilling one or more radial ports or holes 130 within the upstream end of end plug 44' which open to an axial bore (not shown) within that component but identical to bore 48 within end plug 44 of the first embodiment. Additionally, the gas tube 12' includes an appropriate PVC molded plastic tubular body 20' having a downstream end wall 22' with a tapped bore 34 sized to the threaded outer periphery of coupling cylinder 36. The body 20' is provided with a series of longitudinally extending radially inwardly projecting ridges 132 which are circumferentially spaced, and which are sized so as to guide an axially insertable $CO_2$ cartridge 134 whose rear end 134a abuts the end of plug 44' of threaded connecting assembly 16'. At the opposite end of the gas tube body 20', bore 146 of that body is open to the exterior and is threaded as at 136. Threaded bore 136 receives a cylindrical end plug 138 with an enlarged diameter portion 138a which is threaded on its outer periphery at 140. The end plug 138 terminates in a reduced diameter squared portion 138b. The end plug 138 may be threaded into the threaded end of the tubular body 20' by means of an appropriate wrench applied to the squared axially projecting portion 138b.

The opposite end of the end plug 138 is provided with an annular recess 138c within which is formed an annular groove 142. The groove 142 carries a compressible elastomeric o-ring 144 whose outer diameter is larger than the diameter of bore 146 of body 20'. Further, the inner end face 138d of the end plug 138 is provide with an axial hole 146, which carries a pin 148 with its pointed end projecting outwardly of that end plug face 138e. The pin 148 is caused by rotation of end plug 138 to penetrate and puncture a cylindrical seal, shown in dotted lines at 150, which seal 150 closes off the interior of the $CO_2$ cylinder 134.

Once the pressurized gas cylinder 134 is placed in position, the end plug is threaded down, causing it to move from right to left until the pointed pin 148 punctures the $CO_2$ cylinder whereupon, the compressed $CO_2$ gas escapes the gas cylinder as indicated by arrows 152. Compressed gas enters radial holes 130 into the axial bore of the end cap 44' of connecting assembly 16'. The connecting assembly 16' is in all other respects similar to that shown in FIG. 4 and the $CO_2$ gas fills a chamber therein similar to chamber 70. The $CO_2$ pressurized gas cylinder provides a sufficient $CO_2$ charge sufficient to inject 12 10cc charged syringes 18 or a single 10 cc syringe (recharged) 12 times. It may be appreciated, that the end plug 138 once penetration of $CO_2$ cylinder seal 150 takes place can be reverse threaded for a number of revolutions sufficient to back off the pin 148 to insure that the $CO_2$ gas can escape freely from the interior of the $CO_2$ cylinder 134. Further, the hollow interior of the gas tube body 20' defines a gas storage chamber 32' functioning in the same manner as gas storage chamber 32 of the embodiment of FIGS. 1–6, inclusive.

If the gas tubes 12, 12' are of insufficient length to safely permit the operator to approach an animal A for injection, the assembly can be further extended axially by making appropriate threaded connection between the tube valve 28 at the upstream end of the gas tube 20 of the embodiment of FIG. 2 or via the exterior threads 140 on end plug 138 of the gas tube 20' in the embodiment shown in FIGS. 7 and 8 and an extension handle (not shown). In that case, the attachment is grasped and the penetration force exerted from the extension handle through the gas tube 12 or 12' to the syringe holder 14.

What is claimed:

1. A pneumatic hypodermic syringe pole for supporting a tubular hypodermic syringe, said hypodermic syringe comprising a hollow tubular syringe body having a needle at one end, having internally a drug injection chamber communicating with said needle, a plunger within said chamber, sealing off said chamber and being axially displaceable to eject a drug from said drug injection chamber through the needle when displaced in the direction of the needle, an opening within the end of said syringe body opposite said needle for receiving a pressurized gas to displace the plunger axially to effect drug ejection, comprising at least one elongated hollow tube, means defining a gas storage chamber within said at least one hollow tube, one end of said at least one hollow tube forming a handle for manual grasping, the other end of said at least one hollow tube including an axial bore for supporting said hypodermic syringe therein, means for supporting an axially shiftable valve member internally of said at least one hollow tube coaxially with said syringe, said valve member having one end positioned in the path of said movement of said axially displaceable syringe, fluid passage means within said axially displaceable valve aligned within said syringe and being selectively opened or closed off to said gas storage chamber at the end opposite said needle and means for biasing said axially slidable valve member in a direction tending to close off communication between said gas storage chamber and said fluid passage means within said axially slidable valve member such that, an operator by grasping the handle end of said at least one elongated hollow tube and jabbing the needle of said axially displaceable syringe into the body of an animal, causes said syringe to move axially relative to said at least one elongated hollow tube to the extent of completing communication between the hole within the syringe body opposite the needle and the end of the axially displaceable valve member proximate to said syringe thereby forcing said axially shiftable valve member to move against said biasing means and to complete communication between the gas storage chamber and the interior of the syringe behind the plunger such that a charge of pressurized gas is applied to said plunger to force the plunger to move axially within the hypodermic syringe body and to inject the drug from the injection chamber into the body of the animal through and wherein, retraction of the handle by the operator and removal of the needle from the body of the animal automatically causes said valve to close preventing further flow of gas from the storage chamber to said syringe body.

2. The syringe pole as claimed in claim 1, wherein said valve member is of t-shape including a radially enlarged head and a reduced diameter valve stem, said valve stem including an axial bore from the end remote from said valve head towards said valve head and extending over a substantial length thereof, a transverse member within said at least one hollow tube having an axial bore slidably mounting said valve stem, said radially enlarged head abutting one end of said transverse member, a seal carried by one of said head and said transverse member for sealing off said axial bore within said transverse member, said at least one elongated hollow tube axial bore to the side of transverse member remote from said syringe forming a gas storage chamber proximate to said radially enlarged head of said valve, and wherein said hollow stem includes at least one radial hole opening to the interior of said hollow stem and being at an axial position such that upon axial displacement of said valve member against the biasing means said at least one radial hole opens to said gas storage chamber to permit momentary flow of pressurized gas from said gas storage chamber through said at least one radial hole and through said hollow valve stem into the interior of said syringe body.

3. The syringe pole as claimed in claim 2, wherein the end of said at least one elongated hollow tube remote from the end carrying said syringe includes a spring biased normally closed gas pressurization valve opening to the interior of said gas storage chamber permitting periodic gas pressurization from a pressurized air supply source through said normally closed gas pressurization valve.

4. The syringe pole as claimed in claim 3, wherein said normally closed gas pressurization valve comprises an inner tube type valve in the form of a cylindrical fitting having external threads being threaded to and having one end projecting axially outwardly of one end of said at least one elongated hollow tube and wherein, an internally threaded cap is threaded to the projecting end to seal off the inner tube type valve to prevent the escape of gas stored under pressure within said gas storage chamber.

5. The syringe pole as claimed in claim 1, wherein the hollow stem has fixably mounted thereto an annular stop proximate to the end of the hollow stem projectable within the axial hole of said syringe body whereby said annular stop limits insertion of said hollow valve stem internally within the opening within end of the syringe body opposite said needle.

6. The syringe pole as claimed in claim 5, wherein said stop includes a resilient seal ring concentrically surrounding said hollow stem of a diameter in excess of the diameter of the opening within the end of the syringe body to radially seal off the opening of the syringe body during momentary discharge of gas under pressure through said hollow stem into the interior of the syringe body for displacement of the plunger to effect ejection of the drug from the injection chamber through said needle.

7. The syringe pole as claimed in claim 1, wherein said at least one elongated hollow tube includes aligned radial holes within said hollow tube at a position intermediate of said syringe body and the end of said axially slidable valve member and wherein, a stop pin is removably inserted through said aligned radial holes to limit the extent of axial insertion of the syringe during syringe loading of the syringe pole bore at the end of said at least one elongated hollow tube opposite said gas chamber and to prevent inadvertent axial displacement of the axially movable valve member to the extent of causing premature release of pressurized gas from the gas storage chamber to said syringe plunger and premature ejection of the drug stored within the ejection chamber of the syringe body carried thereby.

8. The syringe pole as claimed in claim 1, wherein said at least one elongated hollow tube, at said syringe receiving bore, includes at least one annular recess and a resilient o-ring is carried within each said annular recess for compression between said at least one elongated hollow tube and the outer periphery of said syringe body for frictionally guiding the syringe during insertion into the syringe receiving axial bore of said at least one elongated hollow tube and for frictionally maintaining said syringe in position prior to use of the syringe pole.

9. The syringe pole as claimed in claim 1, further comprising a thin flexible strap having one end fixed to the periphery of said at least one elongated hollow tube near the end of said axial bore carrying said syringe, wherein the opposite end of said thin flexible strap has a small diameter hole fitted to the needle projecting from said syringe and wherein, the length of the strap is such that the end bearing the small diameter hole may be fit to the needle but the strip is short enough so that inadvertently once the syringe is fitted into said at least one hollow tube bore, it cannot fall out due to the connection between the strap and the needle at the end of the syringe.

10. The syringe pole and claimed in claim 1, wherein said at least one elongated hollow tube comprises a first hollow tube acting as said handle and forming a separate gas storage chamber and a second elongated hollow tube forming a syringe holder and wherein, a coupling cylinder is threadably connected at opposite ends to said first and second elongated hollow tubes and said axially slidable valve member is caused by said coupling cylinder is threaded to the end of said second hollow tube opposite that slidably receiving said syringe.

11. The syringe pole as claimed in claim 7, wherein said stop pin removably projects through aligned radial holes within said second elongated hollow tube.

12. The syringe pole as claimed in claim 10, wherein said first elongated hollow tube includes opposed transverse and walls, one of said end walls carries a threaded bore said coupling cylinder is externally threaded and has one end threaded into said threaded bore of said one end wall, the other end wall of said first elongated hollow tube has an internally threaded bore and an end play is threaded into the threaded bore of said other end wall said first elongated hollow tube, said end plug carries an axially projecting pointed pin on an end face thereof interiorly of said first elongated tube, a pressurized gas container is carried internally of said first elongated hollow tube having a sealed end facing said puncture pin, said container abutting a hollow end plug of said coupling cylinder and said compressed gas container being of a length such that the rupturable seal carried at the open end of said pressurized gas of said container is in the path of movement of said pointed end of said puncture pin such that upon initial rotation of said end plug bearing said puncture pin in a direction causing said plug to move axially into said first elongated hollow tube, the seal is punctured whereupon, partial unscrewing of that end plug insures release of the high pressure gas from said pressurized gas container into the interior of said at least said first elongated hollow tube to effect gas pressurization of said gas storage chamber.

* * * * *